(12) United States Patent
Hsieh et al.

(10) Patent No.: US 8,473,038 B2
(45) Date of Patent: Jun. 25, 2013

(54) MOBILE AND WEB-BASED 12-LEAD ECG MANAGEMENT

(75) Inventors: Jui-Chiem Hsieh, Taoyaun (TW); Kuo Chiang Yu, Taoyaun (TW); Hsiu-Chiung Lo, Taoyaun (TW); Chia Chang Hung, Taoyaun (TW); Li-Chern Pan, Taoyaun (TW); Po-Wei Lin, Taoyaun (TW)

(73) Assignee: Yuan Ze University, Taoyaun (TW)

( * ) Notice: Subject to any disclaimer, the term of this patent is extended or adjusted under 35 U.S.C. 154(b) by 862 days.

(21) Appl. No.: 12/467,785

(22) Filed: May 18, 2009

(65) Prior Publication Data

US 2009/0299204 A1     Dec. 3, 2009

(30) Foreign Application Priority Data

May 30, 2008  (TW) .............................. 97120301 A

(51) Int. Cl.
A61B 5/04     (2006.01)

(52) U.S. Cl.
USPC ........................................................ 600/509

(58) Field of Classification Search
None
See application file for complete search history.

(56) References Cited

U.S. PATENT DOCUMENTS

| 6,708,057 | B2* | 3/2004 | Morganroth | 600/509 |
| 7,310,648 | B2* | 12/2007 | Simske et al. | 1/1 |
| 2008/0004904 | A1* | 1/2008 | Tran | 705/2 |

FOREIGN PATENT DOCUMENTS

| TW | 357078 | 5/1999 |
| TW | 363404 | 7/1999 |
| TW | 592127 | 6/2004 |
| TW | 200718396 | 5/2007 |
| TW | I289052 | 11/2007 |

OTHER PUBLICATIONS

Hsin-Yi Lin et al., An ECG Image and Curve Display Environment in DICOM, Journal of Medical and Biological Engineering, Apr. 2004, pp. 29-34, vol. 24 No. S, Journal of Medical and Biological Engineering.

David L. Donoho, De-Noising by Soft-Thresholding, IEEE Transactions on Information Theory, vol. 41, No. 3, May 1995, pp. 613-627.

* cited by examiner

*Primary Examiner* — Eric D. Bertram
*Assistant Examiner* — Elizabeth K So
(74) *Attorney, Agent, or Firm* — WPAT, P.C.; Anthony King

(57) ABSTRACT

The present invention provides a mobile and web-based 12-lead ECG management information system for processing clinical 12-lead ECG, comprising: (a) a clinical device for automatically extracting a SCP-ECG or XML-ECG file and processing signals; (b) an ECG database for saving data exported from the clinical device with web-based user interface, and a mobile database which is synchronized with the ECG database; and (c) an interactive electric document for annotating 12-lead ECG with clinical diagnosis codes.

4 Claims, 16 Drawing Sheets

MOBILE AND WEB-BASED 12-LEAD ECG MANAGEMENT

FIELD OF THE INVENTION

The present invention relates to a mobile and web-based 12-lead ECG management information system.

DESCRIPTION OF PRIOR ART

Computerizing 12-lead electrocardiogram (ECG) and developing its management information system is an important issue for computerizing operating procedures of clinical diagnosis of heart medicine. The major difficulties during the development of computerized 12-lead ECG include: (1) raw ECG signals can not be acquired from clinical ECG measurement instruments such as PHILIPS touch trim and HP Pagewriter series as stated in TW publication No. 200718396, TW patent No. 357078 and TW patent No.592127; and (2) various ECG file formats, such as HP binary SCP-ECG and PHILIPS character mode XML-ECG, are unable to be integrated to facilitate clinical inquiries and management.

Traditionally, browsing, as well as diagnosing or saving, directly through 12-lead ECG instruments needs payment for ECG management information softwares developed by the instrument manufacturers, such as PHILIPS Tracemaster, an ECG management information software developed by PHILIPS, Muse, an ECG browsing software developed by GE, and HP ECG Manager, an ECG management information software developed by HP. These technology could be found in Taiwan patents such as TW patent No. 363404 and TW patent No. I289052. Because 12 lead ECG instrument digital output formats commonly used in hospitals at present, such as Standard Communications Protocol for Computer-Assisted Electrocardiography (SCP-ECG) or Extensible Markup Language Electrocardiography (XML-ECG), are not regulated stringently in the standard formulation, the instrument manufacturers could make private ways of compressing and concealing ECG signals. Only some well-resourced hospitals can afford buying additional model-specific system or hardware provided by the same brand to have electronic ECG diagnosis report information, but to integrate different ECG file formats from different brands is still impossible. Although an international organization OpenECG (www.openecg.net) promotes disclosure of ECG file formats and provides related technical support, such support is limited to the standard SCP-ECG files and can not meet the medical needs of the clinical because that 12-lead ECG instruments used in clinical are only compatible with SCP-ECG file format, and most foreign instrument manufacturers conceal their ways of compressing ECG signals for follow-up commercial benefits on the electronic ECG report browser software. Therefore, many hospitals adopt method of scanning printed ECG reports into image files via manpower, followed by adding DICOM (Digital Imaging and Communications in Medicine) headers to the image files with assistance of PACS (Picture Archiving and Communication Systems) manufacturers, and then the ECG could thus be browsed via PACS. However, scanning via manpower is time-consuming and laborious. Furthermore, the image files are so large that they would waste a lot of storage space and cost, and also could not fit the requirement of Medical Center in academic research due to lack of raw ECG signals (An ECG Image and Curve Display Environment in DICOM, Vol.24 No.S, 2004/04, s29-s34, Journal of Medical and Biological Engineering).

The raw ECG signals in a HP SCP-ECG file are processed by filtering, with bandwidth ranges from 0.5 Hz to 40 Hz complying with the existing standards used in observation of clinical diagnosis. The bandwidth of ECG signals stored in a PHILIPS XML-ECG file ranges from 0.05 Hz to 150 Hz, which belongs to the high-resolution ECG recommended by American Heart Association (AHA). Although bandwidth which ranges from 0.05 Hz to 150 Hz may cover all the spectrum distribution in ECG, it is not feasible for the actual clinical diagnosis based on signal waveform. The waveforms could be interfered by the baseline drift or high frequency noise, particularly ECG characteristics at S-T segment part, and could hardly be recognized for clinical diagnosis. Recent studies has disclosed that the ECG noise could be filtered out by the discrete or stationary wavelet transform, but the ECG signals they used were acquired from MIT-BIH public ECG signal database of single-lead 24-hour ECG recorder. They did not really deal with clinical 12-lead SCP-ECG or XML-ECG files which are largely different from single-lead ECG in signal bandwidth and sampling frequency, so that it is unable to confirm the clinical usefulness of their method (Donoho DL, De-noising by soft-thresholding, IEEE Trans. Information Theory, 1995:613-627).

What's more, pay ECG management information software provided by 12-lead ECG instrument manufacturers only support a simple ECG browse query; diagnosis can not be input, and hospitals are not able to expand its system to get functional modules they need. At present, there is no mobile 12-lead ECG management system which can communicate with clinical 12-lead ECG instruments. Although there is a need in such products clinically, even Philips or HP, the 12-lead ECG instrument manufacturers, does not produce such kind of products.

BRIEF DESCRIPTION OF THE DRAWINGS

FIG. 9 shows that physicians can enter diagnostic information through the web-based interface.

SUMMARY OF THE INVENTION

Figure 1:
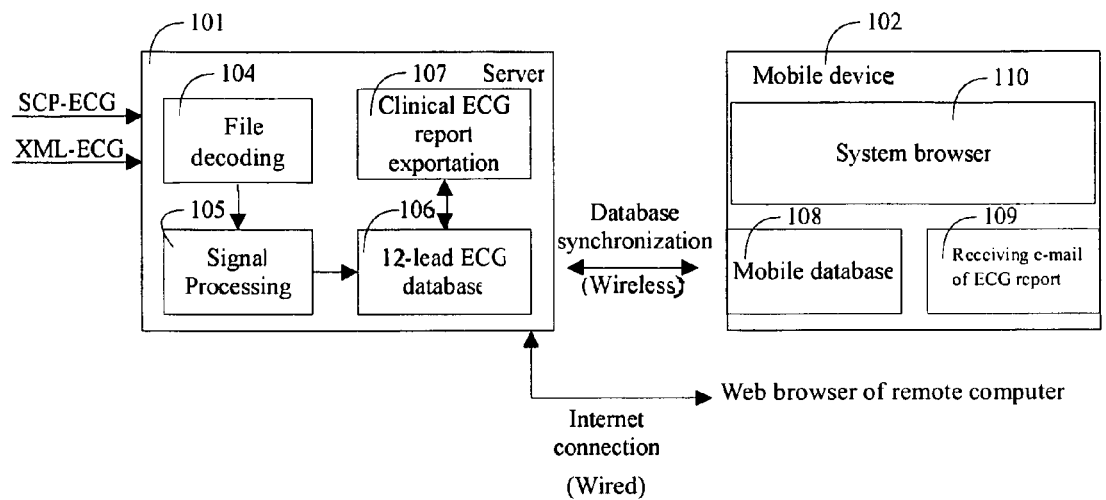
FIG. 1 shows a system architecture diagram.

The present invention relates to a mobile and web-based management information system for processing clinical 12-lead electrocardiogram (ECG), comprising: (a) a clinical device for automatically extracting a SCP-ECG or XML-ECG file and processing signals; (b) an ECG database for saving web-based data exported from the clinical device, and a mobile database which is synchronized with the ECG database; and (c) an interactive electric document for annotating 12-lead ECG with clinical diagnosis codes.

DETAILED DESCRIPTION OF THE INVENTION

The present invention provides a mobile and web-based 12-lead ECG management information system for clinical use. In addition to providing query and diagnosis of 12-lead ECG in the general outpatient services, web-based ECG Management System can also be applied by clinical emergency physicians for transmitting electronic ECG files, biochemical test results or patient symptoms to heart specialist physicians' PDA or cell phone when the heart specialist physicians are not at the hospital or emergency scene, in order to perform common emergency consultation in a timely manner to save the lives of patients. The distant heart specialist physicians can query or browse patients' medical history through handheld mobile devices with wireless network or 3.5G communication, and transmit the diagnostic results or medication information back to the hospital database for synchronous update in order to provide timely, accurate long-distance medical services.

The present invention also provides a system to make an interactive PDF-based 12-lead ECG electronic report, and to satisfy the clinical requirements of practical operation. For example, electronic report diagnosis codes (ICD9), patient's symptoms, biochemical test results and confirmation proved by physicians are all required on the electronic report. The development of interactive PDF e-report can increase the readability for physicians to browse, and also make the exchange of patients' ECG records more convenient.

Therefore, the present invention provides a mobile and web-based management information system for processing clinical 12-lead electrocardiogram (ECG), comprising: (a) a clinical device for automatically extracting a SCP-ECG or XML-ECG file and processing signals; (b) an ECG database for saving web-based data exported from the clinical device, and a mobile database which is synchronized with the ECG database; and (c) an interactive electric document for annotating 12-lead ECG with clinical diagnosis codes.

The device for automatically extracting a SCP-ECG file and processing signals comprises: (a) a device for decoding information of sections 0, 1, 8, and 128; and (b) a device for processing Huffman decoding. The device for automatically extracting a XML-ECG file and processing signals comprises: (a) a device for reading and decoding content of report information (reportinfo tag), data acquisition information (measurements tag), patients' information (patient tag), interpretation information (interpretations tag) and waveforms information (waveforms tag); and (b) a means for processing noise.

Figure 4:
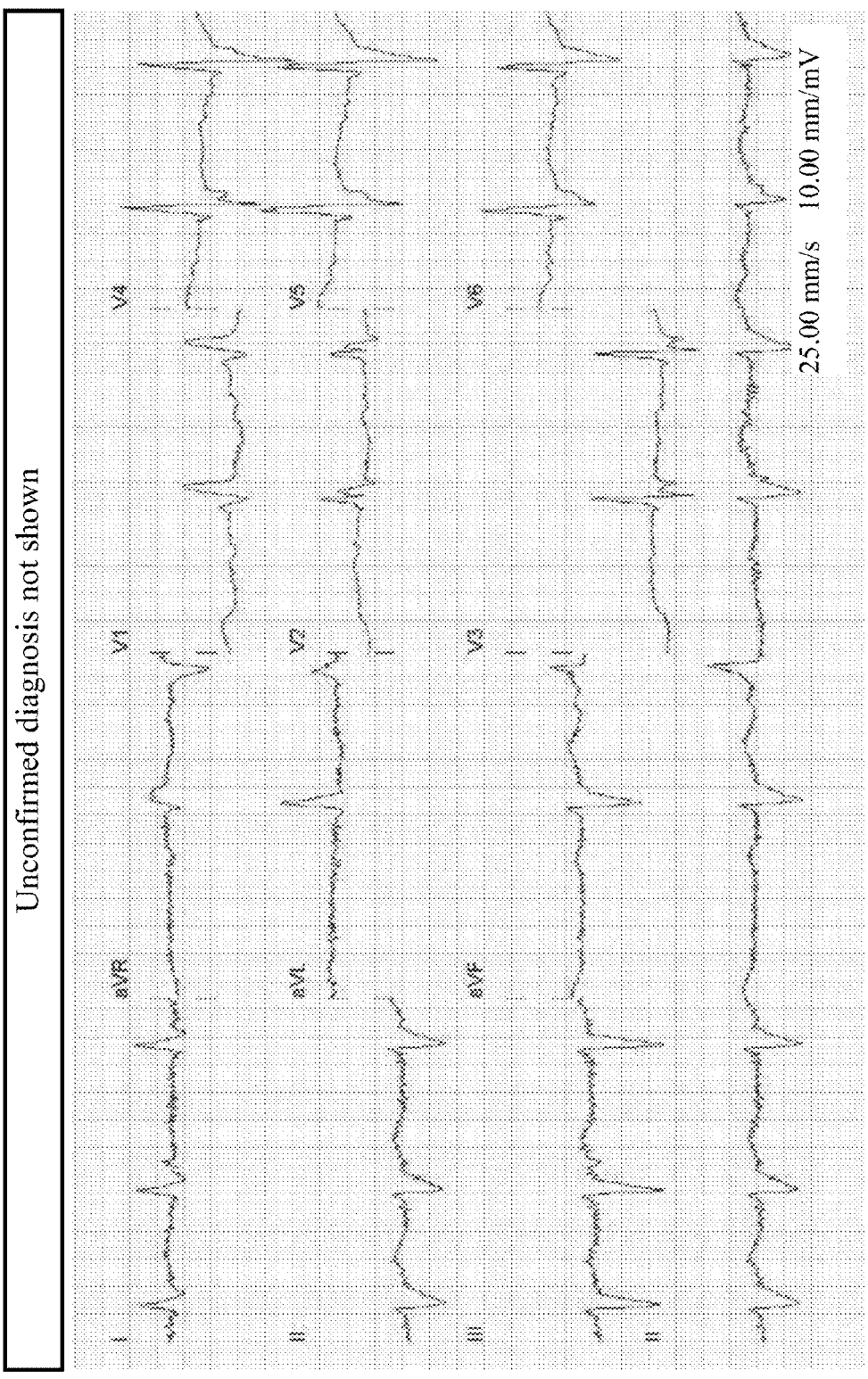
FIG. 4 shows a 12-lead ECG report containing noise.
Figure 5:
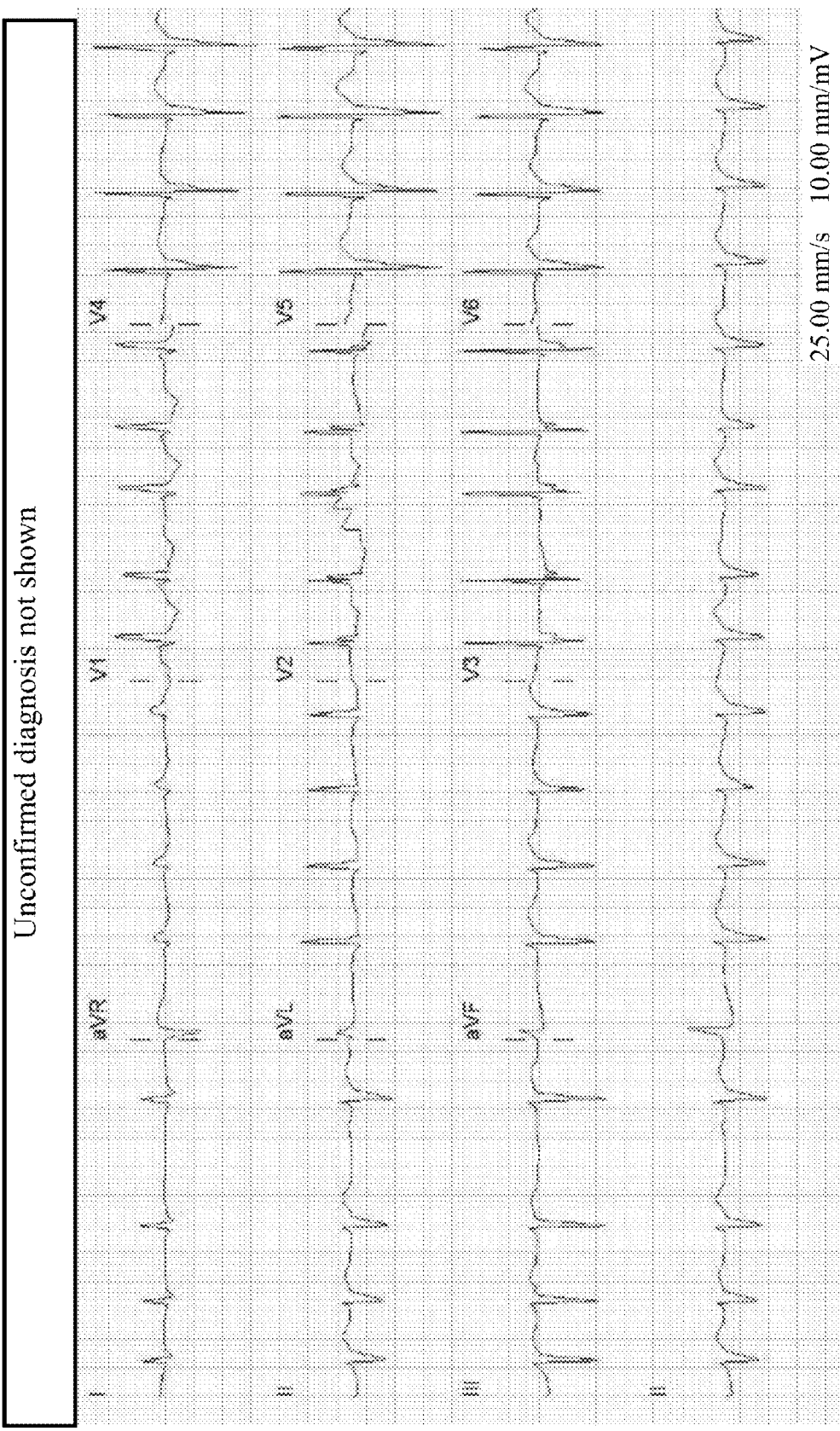
FIG. 5 shows a 12-lead ECG report in which noise has been filtered out.

The means for processing noise filters out interferences due to baseline drift or high frequency noise via stationary wavelet transform. The stationary wavelet transform comprises a formula:

$$ECG(t) = \sum_k a_k \phi(t-k) + \sum_k \sum_j d_{j,k} \Psi(2^j t - k),$$

wherein the ECG(t) means a time sequence of ECG signals; $\Psi$ means a generating function; $\phi$ means a scaling function; $a_k$ means an approximation coefficient of stationary wavelet decomposition at j-level; $d_{j,k}$ means a detail coefficient of stationary wavelet decomposition at j-level, expressed as:

$$d_{jk} = \frac{\text{median}(d_{j,k})}{0.6725}\sqrt{2\ln N} * f, \text{ where}$$

$$f = j+1 \quad \text{if } j = 1 \text{ or } 2$$

$$f = \frac{1}{j+1} \quad \text{if } j > 2;$$

j means a decomposition order; k means a discrete-time transfer; and f means a revised parameter of threshold. Generally, the decomposition order ranges from 1 to 10. Preferably, the decomposition order is 8. In a preferred embodiment of the present invention, the ECG report without process of stationary wavelet transform (FIG. 4) was processed via stationary wavelet transform and the interferences due to baseline drift or high frequency noise wherein were filtered out (FIG. 5).

Figure 6:
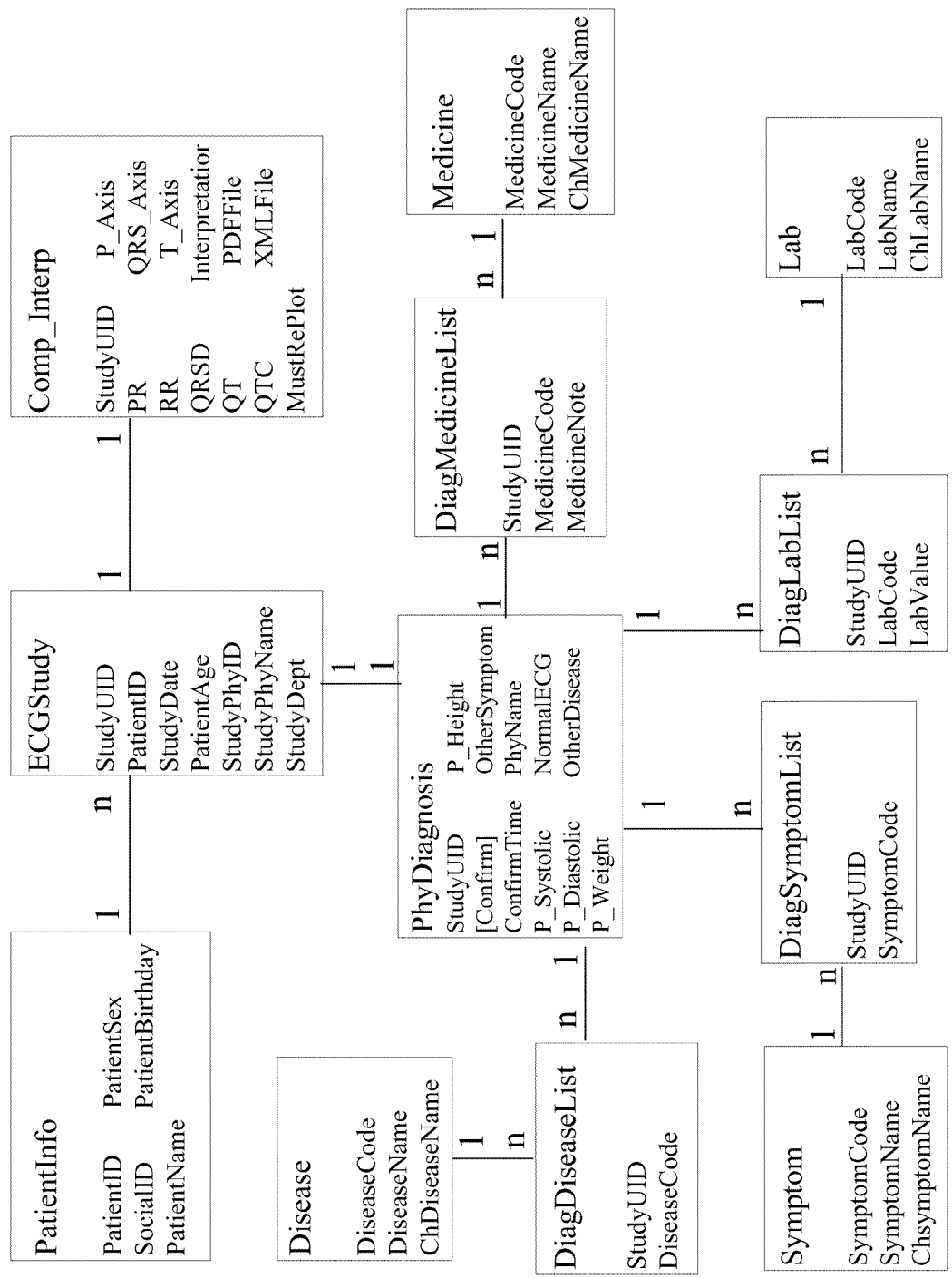
FIG. 6 shows a database architecture diagram.

The ECG database reserves all necessary information of SCP-ECG or XML-ECG files, which mainly comprises 12 tables comprising a patient information table (PatientInfo), ECG study table (EGCStudy), computer interpretation table (Comp_lnterp), physician diagnosis table (PhyDiagnosis), biochemical diagnosis table (DiagLab), medicine information table (DiagMedicine), and symptom description table (DiagSymptom) (FIG. 6). The patient information table comprises patient's name, ID number, gender, and date of birth acquired from HIS. The ECG study table comprises unique document ID (StudyUID) and the original ECG file with information on it, wherein the information comprises date of the examination, age of the patient, the physician ID, the physician name, and the name of department which the physician belongs to. The computer interpretation table mainly comprises computer interpretation extracted from XML-ECG files, including some characteristic parameter values of ECG signals. The physician diagnosis table mainly saves remarks of physician diagnosis, time of diagnosis confirmation, and information of physicians. The biochemical diagnosis table saves blood test result of patients. The medicine information table saves prescription and dosage of medicine for patients. The symptom description table saves symptom description and medical history of patients.

The present invention can reach the following effects:
1. Improving Efficiency and Reducing Waste of Resources
    With the ability to integrate different types and various file formats of 12-lead ECG files, hospitals have no needs to buy model-specific ECG browser which brings inconvenience for managing files and clinical use. The system of the present invention can digitalize patients' ECG and directly send these ECG files to a server for processing and being immediately stored in the 12-lead information management system established by the present invention. It saves a lot of unnecessary operating flow and reduces waste of manpower and paper resources.
2. Security Management
    It is not easy to manage traditional paper ECG and thus the possibility of leaking patient information is very large. When the ECG information is digitalized and performed by computer system, the data could be printed only if it is necessary and with physicians' consent. Therefore, the system of the present invention can reach effective control and decrease risk of information outflow
3. Enhancing the Quality of Medical Care
    Compared with JPG or TIF image format provided by ECG instrument manufacturers, the present invention not only can acquire raw data of ECG signals, but also transfer ECG files into vectorized PDF files which can be browsed on PDA or cell phones. Using PDF files can not only save resources and space but also make graphics not distorted during zoom in or zoon out. Although there has been someone using vector-based SVG graphics, SVG browser in PDA or cell phones are very expensive and not universal.

Mobile medicine, which could be conducted by the system, allows physicians to do remote ECG diagnosis, that is, patients in remote areas can also be diagnosed by more experienced physicians in big citys. Therefore, the quality of medical care is raised. Achieving real-time remote diagnosis can also increase the diagnostic accuracy rate and patient survival rate. At present, the system integrating mobile medicine and long-distance real-time diagnosis has been practically applied in 804 Cardiology of Armed Forces General Hospital. The hospital uses the database and mobile device of the present invention to manage information and to browse and diagnosis respectively. Therefore, the value of the system of the present invention for clinical use is proved 4. Future Development If wireless network can be installed in each ambulance in the future, ECG of patients on the ambulance can be sent to hospitals so that physicians in hospitals can make diagnosis and prepare first aid measures before patients being sent to hospitals. If physicians rich in experience are not in the hospitals, with the mobile database system of the present invention, the ECG can also be sent to the physicians' PDA or cell phones through wireless network or e-mail. The Physicians can also upload their diagnosis result immediately to the database, with which staffs in the hospitals can do early preparation for the patients. Thus, locations are no longer the restrictions on ECG diagnosis from physicians. Further, the 12-lead database can be developed into a digital ECG-learning platform to be a 12-lead knowledge base for studying heart-related diseases. Through this online system, medical interns can be trained for improving their decision-making ability.

EXAMPLES

The examples below are non-limiting and are merely representative of various aspects and features of the present invention.

As shown in FIG. 1, the present invention provided a mobile 12-lead ECG management information system. First, the digital output files, such as HP SCP-ECG or PHILIPS XML-ECG, of clinically frequently used 12-lead ECG instruments were transmitted to the server-side 101 which was synchronized to the mobile device client 102 with internet connection. In addition, the remote computer could be manipulated by the web browser via the network connected to server-side. After the SCP-ECG or XML-ECG files were transmitted to the server, file decoding 104 and further signal processing 105 were carried out. The result was stored in the 12-lead ECG database 106, and was exported as a clinical ECG report 107. The mobile device client database 108 was synchronized to server-side database. The report was received by e-mail 109 and the system browser 110 was used to do further file management. Detailed examples were described below.

Method of Processing SCP-ECG Files

Figure 2:
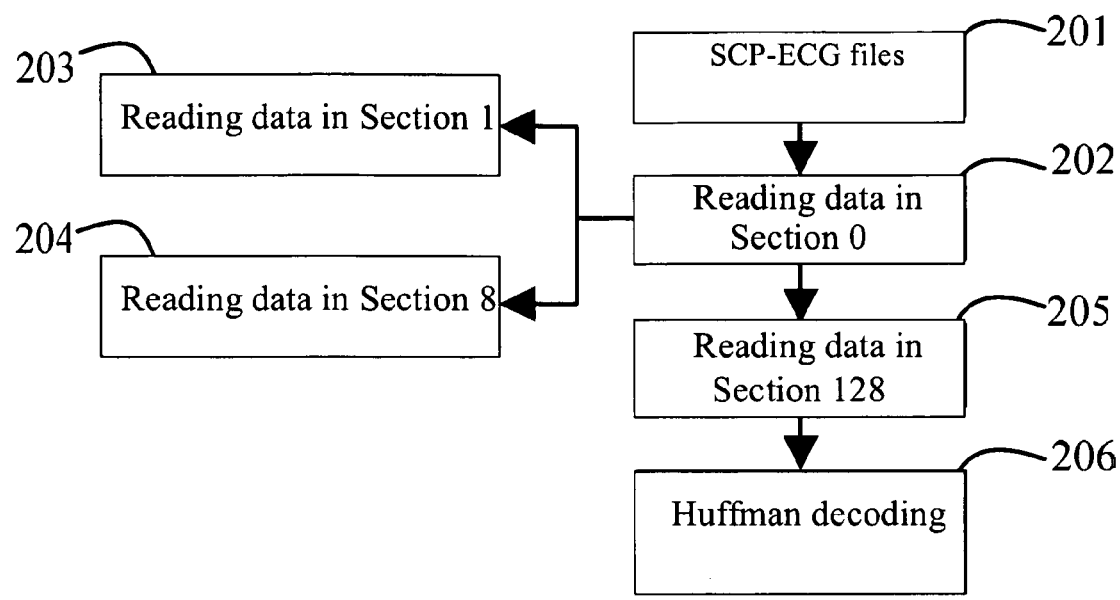
FIG. 2 shows a flow path of decoding HP SCP-ECG.

The method of processing digital output files (SCP-ECG files) of the 12-lead ECG instrument in the present invention was shown in FIG. 2. The clinically used SCP-ECG file format was based on binary and composed of many sections.

The method of processing section 0, section 1, section 8, and section 128 was described as follows.

i. SCP-ECG file format was read 201 to extract data in section 0 202. Section 0 was an indicator pointing to locations of all remaining sections, wherein the sections with non-zero length value and non-zero index value were the parts where information was stored. Each section comprised a tag of 2 bytes, a length value of 4 bytes, and an index value of 4 bytes. Each consecutive byte was read from right high byte to left low byte, wherein their index value was always from 1 to start.

ii. Data of section 1 was extracted 203, wherein the data comprised related information of patients and ECG. Information was arranged in accordance with the method defined by standard SCP, and some self-defined tags were further added in.

iii. Data of section 8 was extracted 204, wherein the data comprised ECG diagnosis and analysis results in text. Information was saved line by line to a total of 17 lines, comprising a tag of 2 bytes (0D0A), a number-of-line value of 2 bytes, a length value of 1 byte, and a following data length part with length value minus two. Text parts were all saved according to ASCII.

iv. Data of section 128 was extracted 205, wherein the data mainly comprised of ECG signals. The data part of ECG signals was divided into 36 tags and an end tag, wherein each tag has its own unique code. Therefore, when the first tag (1D01) was found, the location of the next tag could be calculated in accordance with the length of the first tag. Each data part comprised a tag of 2 bytes, a length value of 2 bytes, and data blocks stored in accordance with the data length; each lead had a main tag (in which ECG signals were stored) and a sub tag. There were a total of 12 short leads, 3 long leads, 6 unused tags and an end tag. The ECG signals could thus be extracted by the following steps: reaching the first tag, retrieving the following 12 pairs of main/sub tags (i.e. 12 short leads), skipping the following 3 tags, retrieving the following 6 pairs of main/sub tags (i.e. 3 long leads), skipping the following 3 tags, and than reaching the end-tag.

v. ECG signals from each lead were first converted into binary format and then decoded by Huffman tables 206. FIG. 2 showed an extraction of continuous 0 at the same time. When nine consecutive 0-bit were in the presence, the next three bits were the length values of saving 0.

Method of Processing XML-ECG Files

Figure 3:
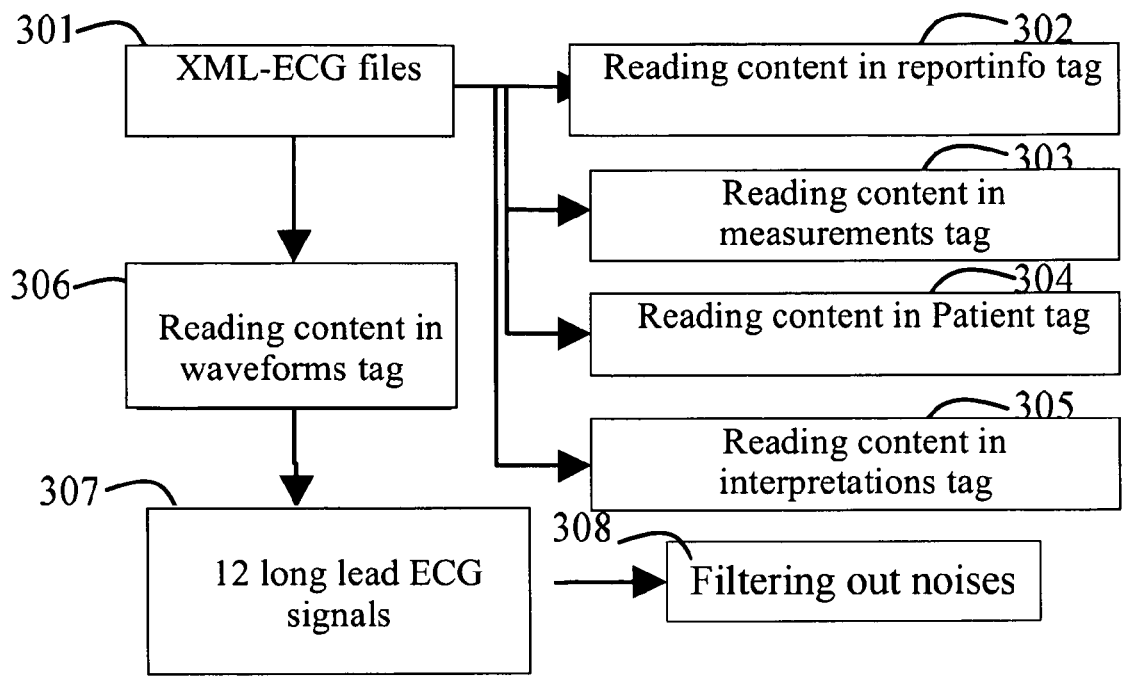
FIG. 3 shows a flow path of decoding PHILLIPS XML-ECG.

The method of processing digital output files (XML-ECG files) of the 12-lead ECG instrument in the present invention was shown in FIG. 3. The clinically used XML-ECG file format was based on ASCII. The method of processing the files was described as follows.

SCP-ECG file format was read 301, and the tag content of reportinfo 302, measurements 303, Patient 304, interpretations 305, and waveforms 306 were continually read out. 12 long lead ECG signals were restored from waveforms tag content by Base64 decoding 307. Finally, the noises were filtered out 308.

Remote computer web browser

Figure 7:
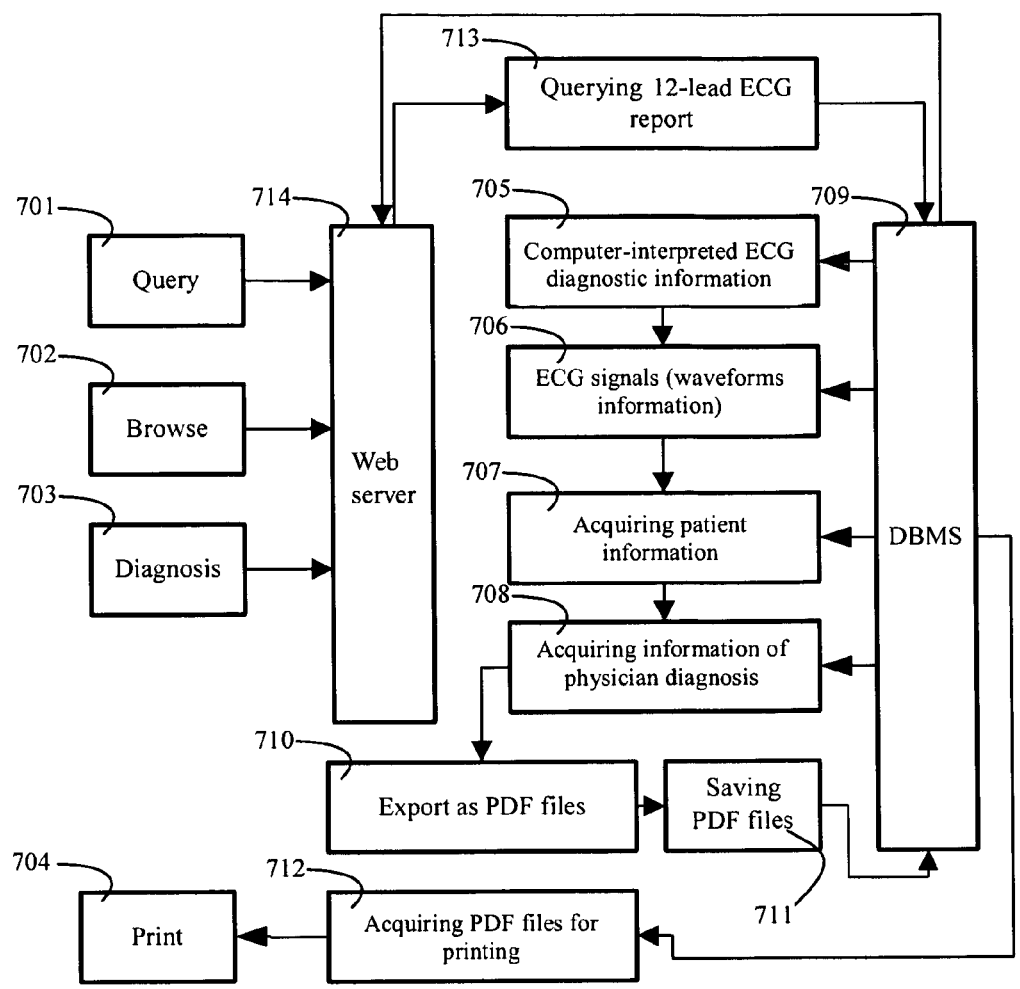
FIG. 7 shows a flow path of implementing web-based 12-lead ECG report.
Figure 8:
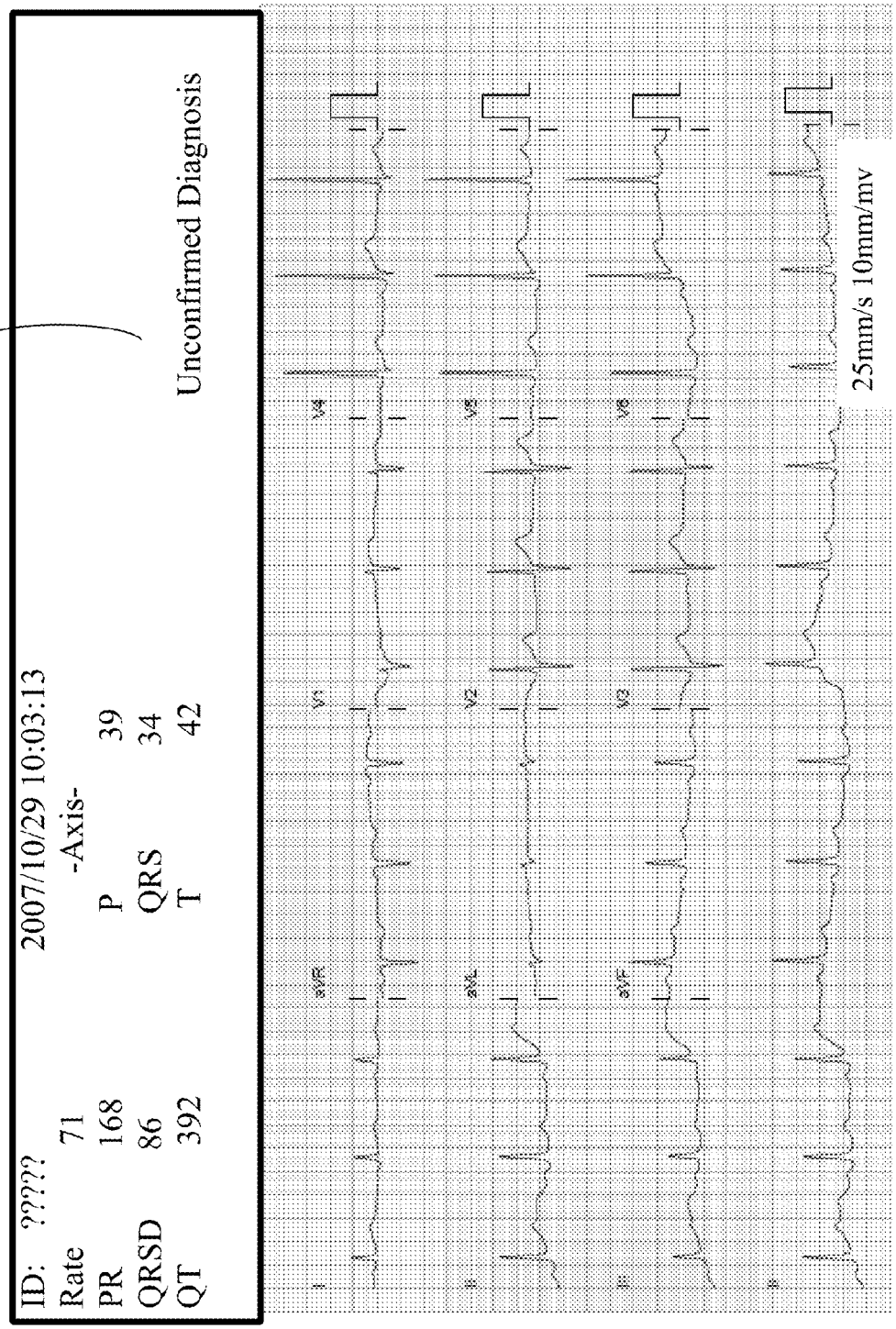
FIG. 8 shows a 12-lead ECG report browser screen without diagnostic notes from physicians.
Figure 9:
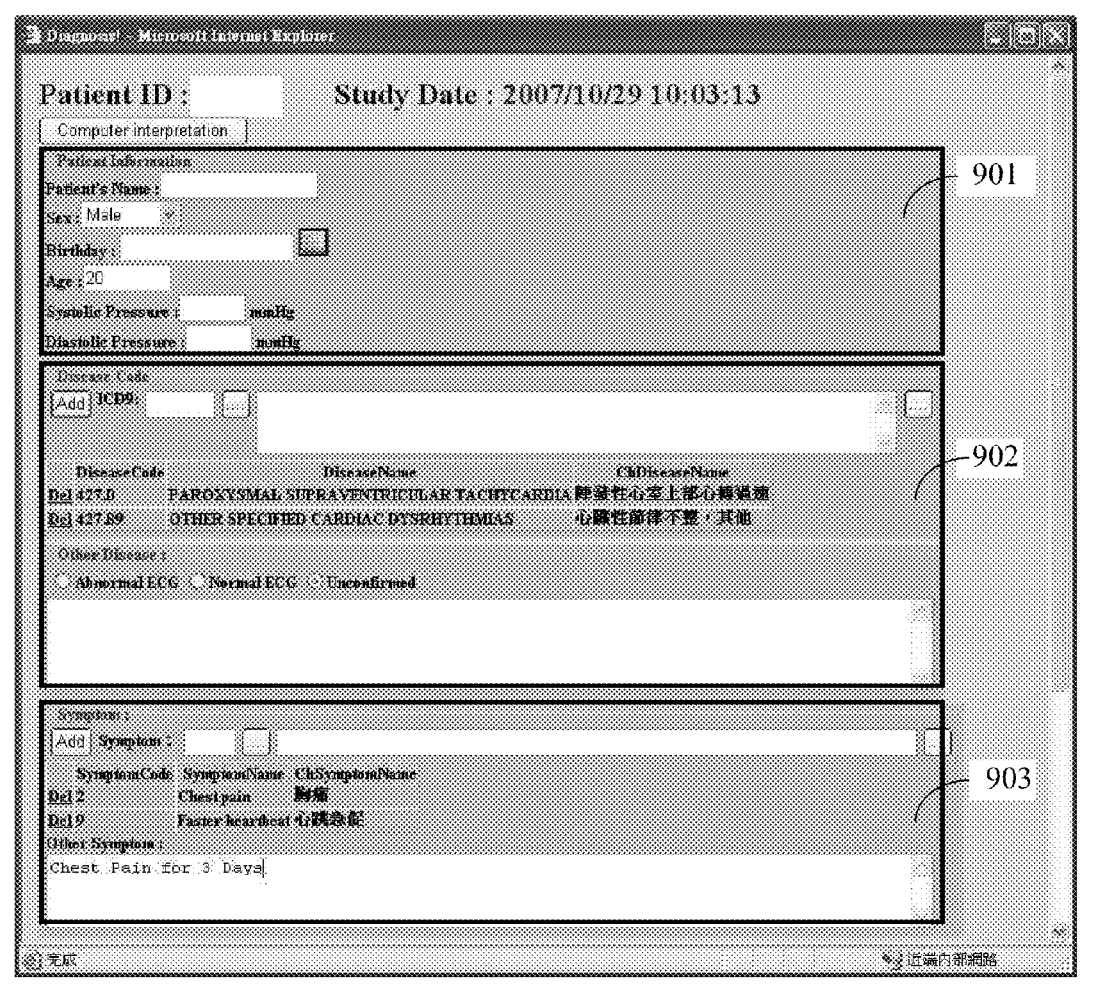
Figure 10:
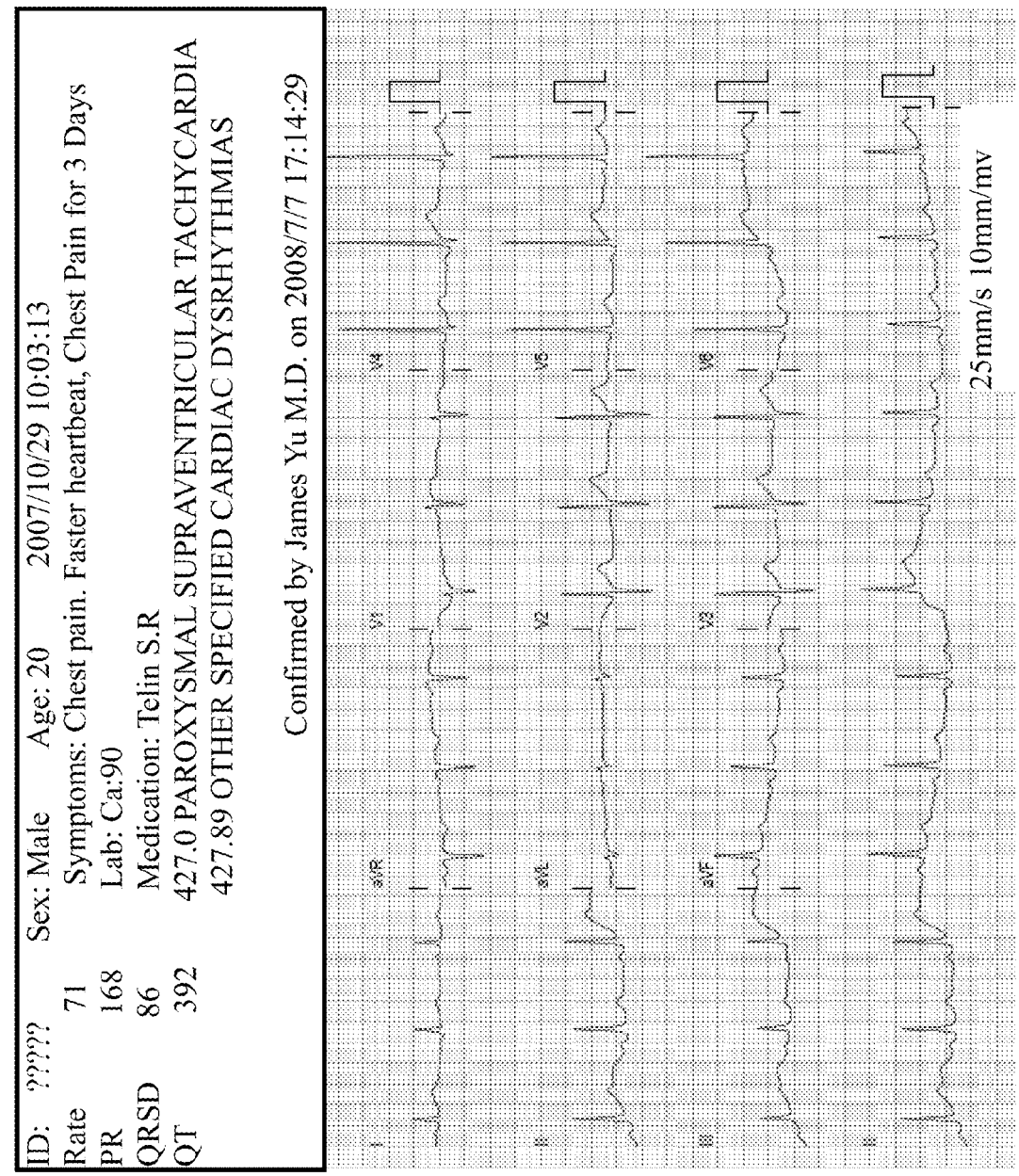
FIG. 10 shows a 12-lead ECG report browser screen with completion of entering diagnostic information by physicians.

FIG. 7 showed the method of browsing, querying, printing, and diagnosing 12-lead ECG report in the present invention. A query for patient's 12-lead ECG report 701 was accomplished by making a query 713 via the web server 714, then the database management system (DBMS) 709 returned related information of the 12-lead ECG report in response to the query. A browse of patient's 12-lead ECG report 702 was also available via the web server 714 by extracting related information of the 12-lead ECG report from DBMS 709. For diagnosis of patient's 12-lead ECG report 703, computer-interpreted ECG diagnostic information 705, ECG signals (waveforms information) 706, patient information 707 and information of physician diagnosis 708 were extracted from DBMS 709 followed by being integrated and transferred into a PDF file format 710 which was saved back in DBMS 709. A print of patient's 12-lead ECG report 704 was acquired through extracting the PDF file from DBMS 709 to print out 712. A 12-lead ECG report browser screen without diagnostic notes 801 from physicians was shown in FIG. 8. Diagnostic information like patient information 901, disease code 902 and symptom 903 was entered by physicians through the web-based interface, as shown in FIG. 9. A 12-lead ECG report browser screen with completion of entering diagnostic information by physicians was shown in FIG. 10. The system automatically redrawn the ECG report to plot diagnosis information in it after that entering of diagnostic information was completed by physicians.

Mobile Device Client System Browser

Figure 11:
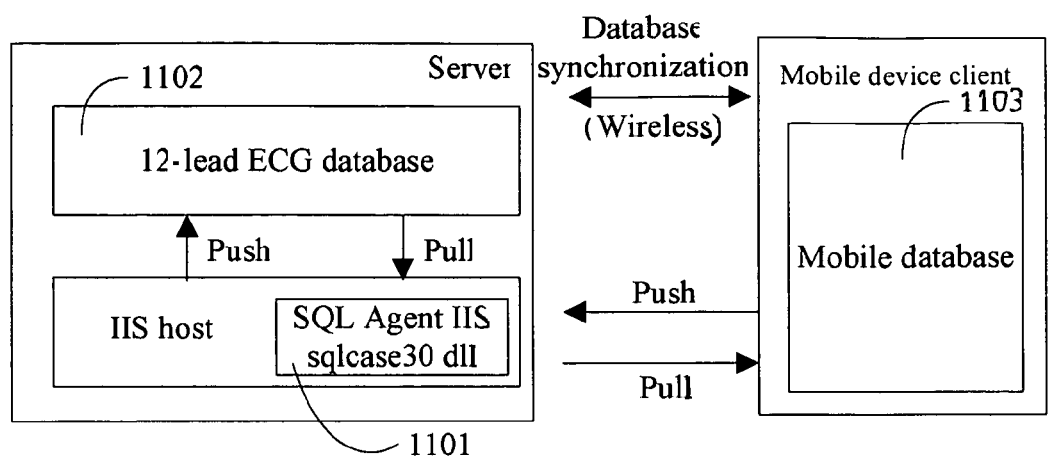
FIG. 11 shows an architecture diagram of synchronizing the mobile device client database and the server database of ECG.

The mobile device client database was synchronized with server database of ECG, as shown in FIG. 11. An element sqlcesa30.dll 1101 on the SQL Agent IIS host was used for performing CRUD 1102 on the 12-lead ECG database, and the results were returned to the original querying PDA for display. Users downloaded queried tables (a table as a unit) from the 12-lead ECG database and saved them to the mobile database 1103 by the PULL instruction of the program in the mobile devices. When the tracking mode was elected (tracking was only required when information needed to be updated and reported back to the server), seven more fields, as shown in Table 1, were added to the downloaded tables to record changes. The downloaded information was revised and uploaded back to original tables in the 12-lead ECG database for updating, by the PUSH instruction of the program in the mobile devices. Changes included deletion or addition. That was, when a data was deleted on PDA and the information tables were uploaded back to the SQL Server by PUSH instruction, the original data in the SQL Server would be deleted due to data synchronization. The multiple subquery was used in PDA to query out the data on the demand. The PUSH instruction was executed automatically just before performing a new query to allow that prior data modified by users could be uploaded back to SQL Server for updating. Thus, the new diagnosis information on PDA would not be overwritten next time when a PULL instruction was executed.

TABLE 1

Tables for recoding changes in mobile database

| Col Name | Type | Description |
|---|---|---|
| _sysIG | INTEGER | The local generation at which the row has been inserted. |
| _sysCG | BIGINT | The generation of the change |
| _sysCD | DATETIME | The time and date the change occurred. |
| _sysP1 | VARBINARY | Custom Property |
| _sysMC | VARBINARY | The bitmap of the changed columns |
| _sysMCS | VARBINARY | The bitmap of the changed columns, saved for change forwarding between sync partners. |
| _sysSR | VARBINARY | Server Reference |

Figure 12:
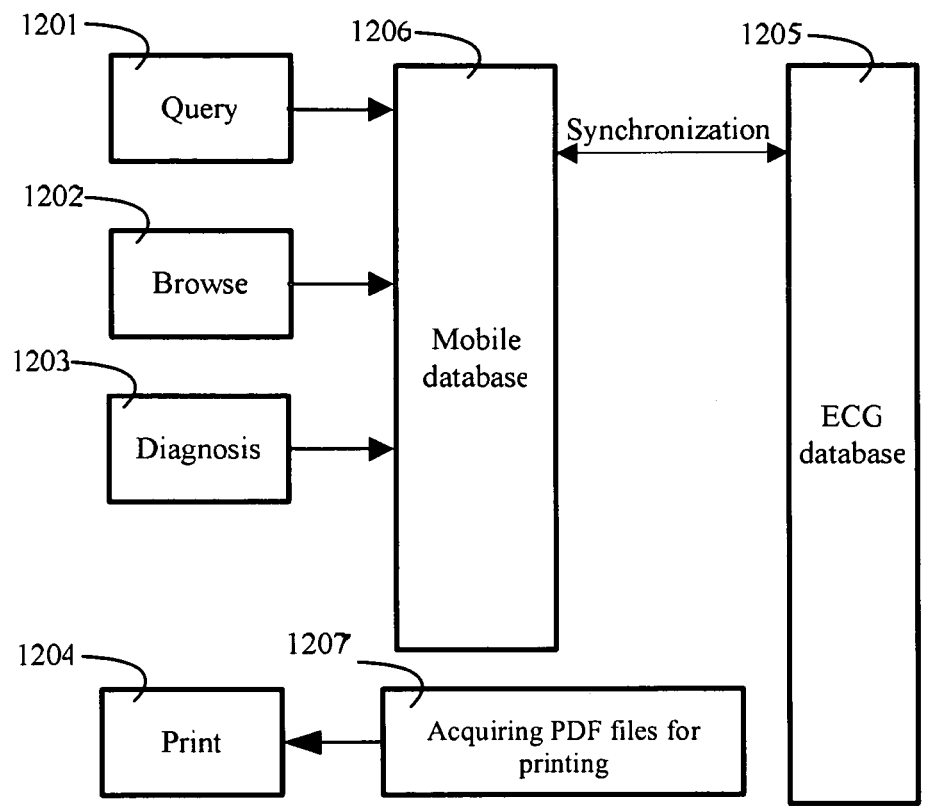
FIG. 12 shows a flow path of implementing the present invention.

FIG. 12 showed the method of browsing, querying, printing, and diagnosing 12-lead ECG report by the mobile device in the present invention. A request for ECG reports could be accomplished by sending a query (entering patient number) from a mobile device PDA. Then, the mobile database 1206 was synchronized with the 12-lead ECG database 1205 in the server. After synchronization, the personal mobile device PDA made its own database similar to the 12-lead ECG database, which could be used in browsing or diagnosing patients' 12-lead ECG reports. The mobile device was also connected to network printer with Bluetooth support via wireless Bluetooth to print ECG reports 1204. The PDF file of 12-lead ECG could further be received by e-mail. First, the mobile device PDA was connected to the internet, and then the built-in software in the system was used to receive PDF files of 12-lead ECG and browse them directly.

Figure 13:
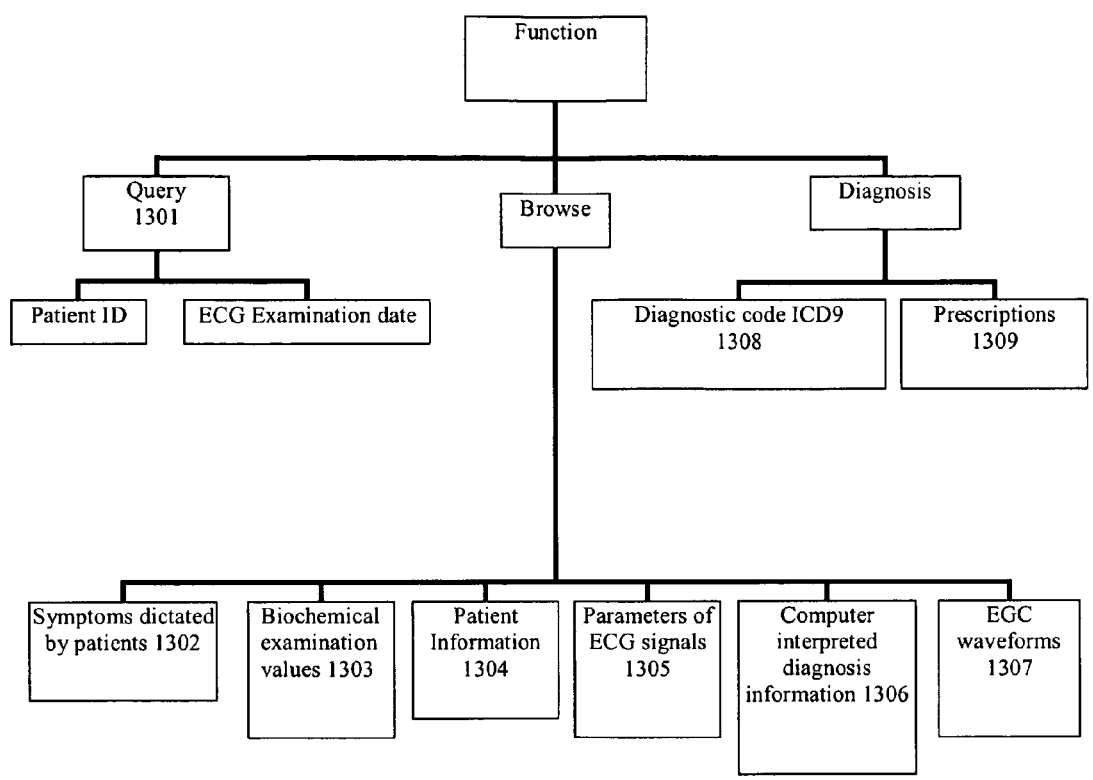
FIG. 13 shows a functional architecture diagram.
Figure 14A:
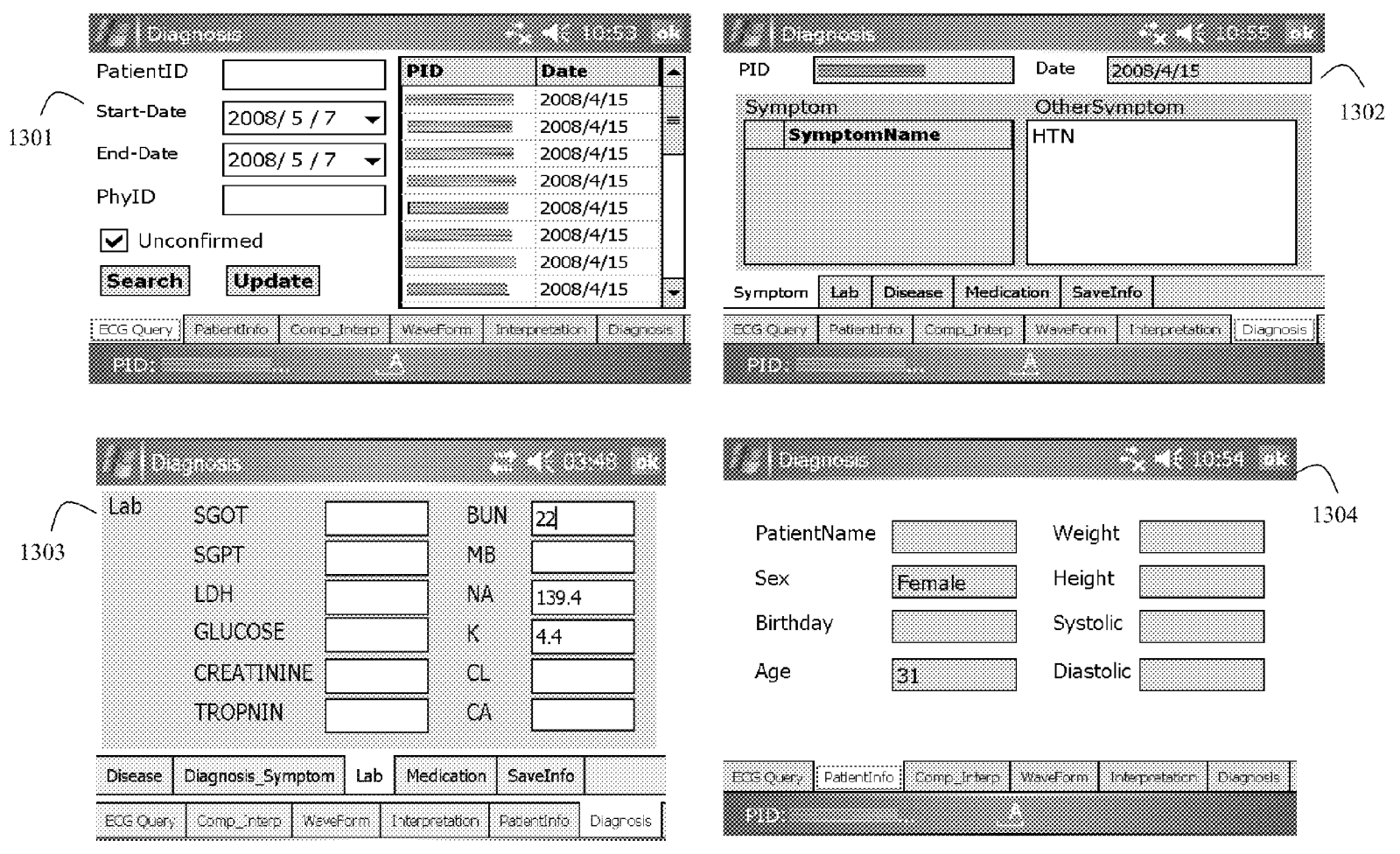
Figure 14B:
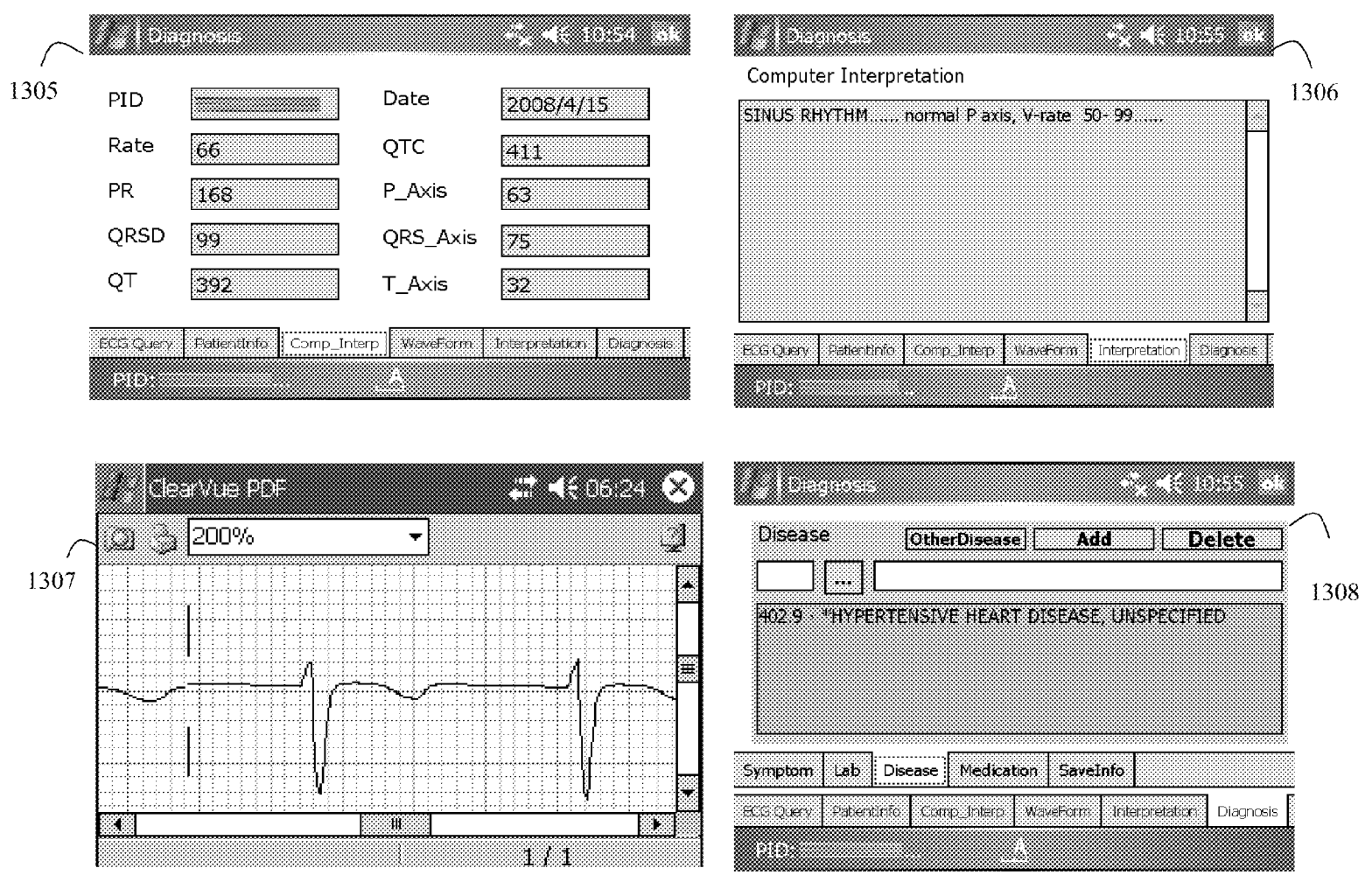
Figure 14:
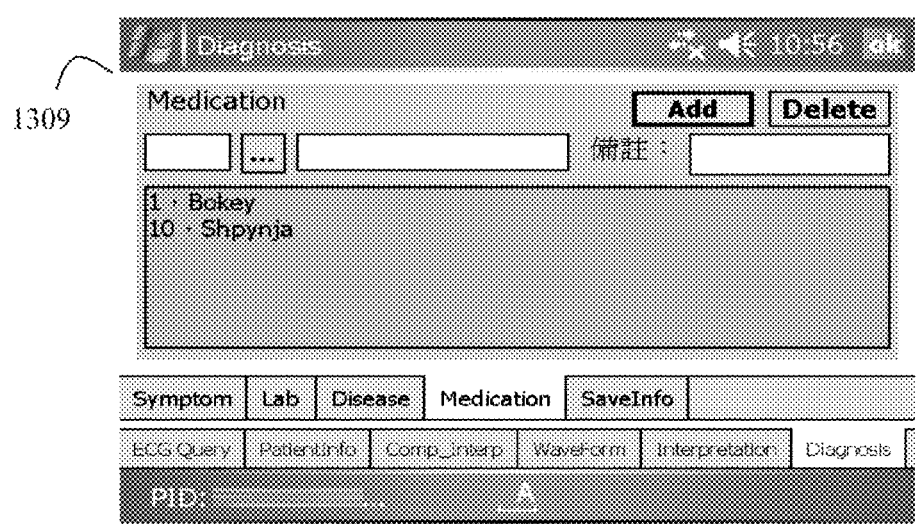
FIGS. 14A, 14B and 14C show a browser or diagnostic screen for mobile device.

Functional interfaces for searching, browsing 1301, diagnosing and printing by users were developed on the mobile device as shown in FIG. 13, a functional architecture diagram. The actual use of the interfaces was shown in FIGS. 14A, 14B and 14C. An user could download the queried tables to the mobile database by the PULL instruction on the wireless access device for browsing data as symptoms dictated by patients 1302, biochemical examination values 1303, patient Information 1304, parameters of ECG signals 1305, computer interpreted diagnosis information 1306 or EGC waveforms 1307. After completion of diagnosis by physicians with the data on PDA, diagnostic results, diagnostic code ICD9 1308 and prescriptions 1309 were first uploaded to the mobile database, and then uploaded back to the ECG database in the hospital for real-time updating by the PUSH instruction on the wireless access device. Therefore, the purpose of mobile medicine was achieved.

The present invention fulfilled the requirements for remote, real-time diagnostic service.

The functions of current major ECG management systems (possessing more than 85% of the domestic market in 12-lead ECG instruments) were compared with the functions of the present invention, as shown in Table 2.

TABLE 2

Functional comparison among different ECG management systems

| | Raw ECG digital signals | Integration | File format for ECG exporting | Diagnosis input | Quert with disease classification | Synchronous mobile query/diagnosis | Expandability |
|---|---|---|---|---|---|---|---|
| HP ECG Manager (Single user license) | N/A | | Reading HP SCP-ECG file format only | TIF | N/A | N/A | X | N/A* |

TABLE 2-continued

Functional comparison among different ECG management systems

| | Raw ECG digital signals | Integration | File format for ECG exporting | Diagnosis input | Query with disease classification | Synchronous mobile query/ diagnosis | Expandability |
|---|---|---|---|---|---|---|---|
| PHILIPS Tracemaster (Network shareable) | Optional | Reading PHILIPS XML-ECG file format only | TIF JPG SVG (Optional) | N/A | N/A | X | N/A* |
| 12-lead ECG management system provided by the present invetion (Network/ mobile devices synchronously sharable) | Yes | Reading both HP SCP-ECG and PHILIPS XML-ECG File formats | PDF | Supporting input of clinical diagnosis codes (ICD9) | Yes | Yes | Yes# |

*Hospitals could not develop expansion modules required due to the private database.
Hospitals could easily develop expansion modules based on clinical requirements.

What is claimed is:

1. A mobile and web-based management information system for processing clinical 12-lead electrocardiogram (ECG), comprising:
    (a) a clinical device for automatically extracting an XML-ECG file and processing signals;
    (b) an ECG database for saving web-based data exported from the clinical device, and a mobile device client database which is synchronized with the ECG database; and
    (c) an interactive electric document for annotating 12-lead ECG with clinical diagnosis codes,
    wherein the device for automatically extracting the XML-ECG file and processing signals comprises:
        (a1) a device for reading and decoding content of report information (reportinfo tag), data acquisition information (measurements tag), patients' information (patient tag), interpretation information (interpretations tag) and waveforms information (waveforms tag); and
        (b1) a means for processing noise,
    wherein the means for processing noise filters out interference due to baseline drift or high frequency noise via stationary wavelet transform comprising a formula:

$$ECG(t) = \sum_{k} a_k \phi(t-k) + \sum_{k}\sum_{j} d_{j,k} \Psi(2^j t - k)$$

where

ECG(t) means a time sequence of ECG signals;

$\psi$ means a generating function;

$\phi$ means a scaling function;

$a_k$ means an approximate coefficient of stationary wavelet decomposition at j-level;

$d_{j,k}$ means a detail coefficient of stationary wavelet decomposition at j-level, and expressed as:

$$d_{jk} = \frac{\text{median}(d_{j,k})}{0.6725} \sqrt{2\ln N} * f, \text{ where}$$

$$f = j+1 \quad \text{if } j = 1 \text{ or } 2$$

$$f = \frac{1}{j+1} \quad \text{if } j > 2;$$

j means a decomposition order;

k means a discrete-time transfer; and f means a revised parameter of threshold.

2. The system of claim 1, wherein the signals are processed as decoded raw waveforms.

3. The system of claim 1, wherein the decomposition order ranges from 1 to 10.

4. The system of claim 1, wherein the decomposition order is 8.

* * * * *